(12) United States Patent
Atanasoska et al.

(10) Patent No.: US 7,365,126 B2
(45) Date of Patent: Apr. 29, 2008

(54) MEDICAL DEVICE ARTICLES FORMED FROM POLYMER-INORGANIC HYBRIDS PREPARED BY ESTER-ALKOXY TRANSESTERIFICATION REACTION DURING MELT PROCESSING

(75) Inventors: Liliana Atanasoska, Edina, MN (US); Michele Zoromski, Minneapolis, MN (US); Robert Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 245 days.

(21) Appl. No.: 11/229,086

(22) Filed: Sep. 16, 2005

(65) Prior Publication Data

US 2007/0066764 A1 Mar. 22, 2007

(51) Int. Cl.
*C08F 8/00* (2006.01)
(52) U.S. Cl. ............... 525/100; 428/447; 428/507; 525/330.3; 525/330.6; 525/342; 525/446; 604/35; 604/264; 604/265
(58) Field of Classification Search ........... 525/446, 525/100, 330.3, 330.6, 342; 428/447, 507; 604/35.7, 264, 265, 280, 35
See application file for complete search history.

(56) References Cited

U.S. PATENT DOCUMENTS

| | | | |
|---|---|---|---|
| 3,646,155 A | 2/1972 | Scott | 260/827 |
| 3,950,285 A | 4/1976 | Wolgemuth | 260/18 |
| 4,574,133 A | 3/1986 | Umpleby | 524/147 |
| 4,753,992 A | 6/1988 | Umpleby | 535/100 |
| 5,336,731 A | 8/1994 | Ondrus et al. | 525/370 |
| 5,556,383 A | 9/1996 | Wang et al. | 604/96 |
| 5,714,257 A | 2/1998 | Shah et al. | 428/391 |
| 5,830,182 A | 11/1998 | Wang et al. | 604/96 |
| 5,951,941 A | 9/1999 | Wang et al. | 264/523 |
| 6,146,356 A | 11/2000 | Wang et al. | 604/96 |
| 6,444,324 B1 | 9/2002 | Yang et al. | 428/447 |
| 6,569,958 B1 | 5/2003 | Gross et al. | 525/446 |
| 6,946,174 B1 | 9/2005 | Chen | 428/35.7 |
| 2005/0015105 A1 | 1/2005 | Chefitz | 606/151 |

FOREIGN PATENT DOCUMENTS

| | | |
|---|---|---|
| JP | 09165441 | 6/1997 |
| WO | WO 98/05269 | 2/1998 |
| WO | 00/48552 | 8/2000 |
| WO | 00/55213 | 9/2000 |
| WO | WO 2005/014075 | 2/2005 |
| WO | 2005/087284 | 9/2005 |

OTHER PUBLICATIONS

C. Lacroix et al., "Properties of PETG/EVA blends: 2. Study of reactive compatibilization by n.m.r. spectroscopy and linear viscoelastice properties," Polymer vol. 37 No. 14, (1996) 2949-2956.
Sang-Hoon Rhee, "Bone-like apatite-forming ability and mechanical properties of poly($\epsilon$-caprolactone)/silica hybrid as a function of poly($\epsilon$-caprolactone) content," Biomaterials 25 (2004) 1167-1175.
V. Bounor-Legare et al., "New transesterification between ester and alkoxysilane groups: application to ethylene-co-vinyl acetate copolymer crosslinking," Polymer 43 (2002) 6085-6092.
V. Bounor-Legare et al., "A new route for organic-inorganic hybrid material syntheses through reactive processing without solvent," Polymer 45 (2004) 1485-1493.
V. Bounor-Legare et al., "Ethylene-co-vinyl acetate copolymer crosslinking through ester-alkoxysilane exchange reaction catalyzed by dibutyltin oxide: mechanistic aspects investigated through model compounds by multinuclear NMR spectroscopy," Polym. Int. 53: 484-494 (2004).
Y. Goutille et al., "Crosslinking in the melt of EVA using tetrafunctional silane: gel time from capillary rheometry," Polymer 44 (2003) 3165-3171.
U.S. Appl. No. 09/689,139, filed Oct. 12, 2000, Chen.
U.S. Appl. No. 11/094,638, filed Mar. 30, 2005, Atanasoska et al.
U.S. Appl. No. 11/213,177, filed Aug. 26, 2005, Atanasoska et al.
U.S. Appl. No. 11/235,743, filed Sep. 27, 2005, Zoromski et al.

*Primary Examiner*—Bernard Lipman
(74) *Attorney, Agent, or Firm*—Vidas, Arrett & Steinkraus

(57) ABSTRACT

A shaped medical device article prepared from a polymer melt composition comprising a polymer ester, a transesterification catalyst, and a tri- or tetraalkoxy silane, by forming and solidifying said composition, and after solidification, subjecting the composition to reaction conditions to effect hydrolysis at least some alkoxysilyl groups remaining in the composition to form silanol groups and to effect condensation of said silanol groups to form a ceramic network. The polymer ester may be a vinyl ester homopolymer or copolymer, or a polymer having ester groups in the backbone thereof.

25 Claims, No Drawings

US 7,365,126 B2

MEDICAL DEVICE ARTICLES FORMED FROM POLYMER-INORGANIC HYBRIDS PREPARED BY ESTER-ALKOXY TRANSESTERIFICATION REACTION DURING MELT PROCESSING

BACKGROUND OF THE INVENTION

It is desirable to identify materials that can provide novel physical properties to medical devices or components thereof, such as catheters and balloons, and that can be integrated in to existing processing regimes. For instance balloons for medical devices such as angioplasty catheters, stent delivery catheters and the like are typically formed by a process of extruding a tube of thermoplastic polymer and then blowing the tube into a balloon at a temperature between Tg (higher temp Tg in case of block copolymers) and melt. Sometimes the blown balloons are held at a temperature above blowing temperature to increase crystallinity of the polymer and dimensional stability of the balloon. The present invention provides hybrid organic polymer-inorganic ceramic materials whose processing can be integrated into such a processing regime.

In U.S. Pat. No. 3,646,155, there is described silanized polyolefins that have hydrolyzable silane moieties linked thereto by free radical reaction and that can be crosslinked by exposure to moisture and a condensation catalyst.

U.S. application Ser. No. 09/689,139, describes a medical device comprising a dilatation balloon formed from a crosslinked polymeric material, the crosslinked polymeric material comprises the reaction product of at least one polymer and at least one hydrolyzable silane having the following general structure:

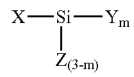

where X is a monovalent non-hydrolyzable organic moiety comprising at least one functional group W which is reactive with said polymer with the proviso that an Si—C bond is present between Si and W, Y is a hydrolyzable group, Z is a monovalent hydrocarbon group, and m is an integer from 1 to 3. The hydrolyzable silane groups, Y of the silane are then activated with moisture to form a crosslinked polymeric material.

U.S. patent application Ser. No. 11/094,638, incorporated herein by reference in its entirety, describes organic-inorganic hybrid materials for use in medical devices that comprise an organic polymer and a sol-gel derived ceramic.

SUMMARY OF THE INVENTION

The present invention in some aspects pertains to medical device articles, for instance medical device balloons, formed from specific hybrid materials and processes for obtaining the same. In other aspects the invention pertains to novel organic-inorganic hybrid materials, methods of preparing same and articles obtained therefrom.

In accordance with the present invention hybrid polymer-ceramic precursor compositions may be prepared in molten state, without the presence of solvent. The prepared compositions can be integrated into conventional thermoplastic polymer processing such as extrusion or injection molding, following which the compositions are processed to form an inorganic ceramic phase without dissolution or dispersion in a solvent.

In one aspect the invention is directed to a shaped medical device or component thereof prepared from a polymer melt composition comprising a polymer ester, a transesterification catalyst, and at least one trialkoxysilane or tetraalkoxysilane, by forming and solidifying said composition, and after solidification, subjecting the composition to reaction conditions to effect hydrolysis of at least some alkoxysilyl groups remaining in the composition to form silanol groups and to effect condensation of said silanol groups to form a ceramic network.

In another aspect the invention in directed to a method of forming a shaped medical device or component thereof comprising providing a polymer melt composition comprising
a polymer ester,
a transesterification catalyst, and
at least one trialkoxysilane or tetraalkoxysilane,
forming and solidifying said composition, and after solidification,
subjecting the composition to reaction conditions to effect hydrolysis of at least some alkoxysilyl groups remaining in the composition to form silanol groups and to effect condensation of said silanol groups to form a ceramic network.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

As used herein the term "polymer ester" pertains to polymers having pendant ester groups, and to polymers having ester groups in the backbone thereof.

Hybrid organic-inorganic compositions prepared by melt blending ethylene-vinyl acetate copolymers with a tetraalkoxy silane and dibutyl tin oxide as transesterification catalyst, followed by extrusion and then hydrolysis/condensation to produce a hybrid material with good elastic and strength properties are described in V. Bounor-Legare, et al., Polymer 43 (2002) 6085-6092; V. Bounor-Legare, et al., Polymer 45 (2004) 1485-1493; V. Bounor-Legare, et al., Polym. Int. 53: 484-494 (2004); and Y. Goutille, et al., Polymer 44 (2003) 3165-3171. Compositions as described in these documents may be employed in the invention.

The polymer esters employed in the invention may be homopolymers or copolymers of vinyl acetate or of other vinyl esters, for instance, vinyl propionate, vinyl butyrate and vinyl benzoate. Mixtures of vinyl esters may be employed. The vinyl ester polymers and copolymers may be partially hydrolyzed.

For copolymers of vinyl esters, other vinyl or vinylidene monomers may be employed. Particular monomers with which the vinyl ester monomer may be employed include olefin and/or cycloolefins including alpha-olefins of the formula $CH_2{=}CH(CH_2)_aH$ wherein a is an integer of 2 or more. Examples of such olefin and cycloolefin monomers include, for instance ethylene, propylene, 1-butene, 2-butene, 1-hexene 1-octene, 1-pentene, 1-tetradecene, cyclopentene, cyclohexene, vinylcyclohexane, cyclopentene, cyclobutene, norbornene, substituted norbornene, and fluorinated olefin and cyclolefin monomers. Still other monomers that may be copolymerized therewith include vinyl aromatic monomers, such as styrene and α-methyl styrene, vinyl chloride, vinyl pyrrolidone, acrylamide, N-methylacrylamide, N-vinylacetamide, vinyl sulfonic acid or a salt thereof (e.g. sodium vinyl sulfonate), acrylonitrile, vinyl ketones, and vinylidene chloride. The vinyl ester content of the copolymer may be from about 1% to 99% by weight, for instance 1-34%, 35-79% or 80-99.5% by weight.

A catalyst that is preferential to transesterification over condensation is employed with the vinyl ester polymer. Dialkyl tin oxides, such as dibutyl tin oxide or dioctyl tin oxide are examples transesterification catalyst. Distannoxane catalysts such as 1-alkoxy-3-acyloxy tetrabutyldistanoxanes may also be used. The catalyst level may be as low as 0.1 mole % relative to ester moieties on the polymer, for instance 0.5-5 mole %.

The melt blend composition of vinyl ester polymer and transesterification catalyst also includes at least one alkoxysilane having three or four alkoxy groups per molecule as a ceramic precursor. Examples of tetraalkoxysilanes include tetramethoxysilane, tetraethoxysilane, tetrapropoxysilane, and tetraisopropoxysilane. Trialkoxysilanes, include trialkoxyalkylsilanes in which the alkyl group is unsubstituted such as trimethoxymethylsilane, triethoxymethylsilane, trimethoxyethylsilane, and the like, trialkoxyalkylsilanes in which the alkyl group is optionally substituted with an aromatic hydrocarbon group, with one or more halogen atoms or with an organic functional group having one or more oxygen, nitrogen or sulfur atoms thereon, trialkoxyarylsilanes in which the aryl group is unsubstituted, for instance triethoxyphenylsilane, and trialkoxyarylsilanes in which the aryl group is optionally substituted with an aliphatic hydrocarbon group, with one or more halogen atoms or with an organic functional group having one or more oxygen, nitrogen or sulfur atoms thereon. A trialkoxyfluoroalkylsilane may be used for instance to as tailor the tribological properties of the material.

In addition to the silicon alkoxide other ceramic precursor compounds of the metals or semi-metals silicon, zirconium, titanium, aluminum, tin, hafnium, rubidium, bismuth, strontium, tantalum, molybdenum, tungsten, rhenium and/or iridium that can form oxides of such metals or semimetals by a hydrolysis/condensation sequence can be incorporated into the composition. Typically such ceramic precursor compounds are also alkoxides, however other compounds are known that can be hydrolyzed to form hydroxides of the metal or semimetals and such compounds may also be employed in the invention. The use of titanium propoxides, zirconium propoxides or other metal alkoxides may provide specific physicochemical properties, such as radioopacity or tensile strength.

In the melt, transesterification between the ceramic precursor alkoxide compound(s) and pendent ester groups of the polymer is initiated after an induction time. This reaction begins in the melt stage, but with a sufficient induction time before gellation to allow for the material to be successfully extruded or injection molded into a shaped article. Loss of volatile acetate ester accompanies the crosslinking reaction with a vinyl ester polymer or copolymer.

Upon first crosslinking the material may loose strength and become quite brittle as well. However, after initial shaping it is further processed to hydrolyze and condense unreacted alkoxy and/or other hydrolyzable groups of the ceramic precursor to form a ceramic network in the compositions. This can be done by treatment with steam or liquid water followed by drying. The residual transesterification catalyst, in the presence of water may be sufficiently catalytic to efficiently effect the hydrolysis of remaining alkoxy groups to silanol groups and then condensation thereof to produce the ceramic network. However, if desired an acid or amine or other known catalyst may be added with the water to catalyze the hydrolysis and condensation reactions. The result is a shaped article of a hybrid material that has good elastic and strength properties and a battery of unusual molecular transport, thermal stability, or other properties provided by the hybrid polymer/ceramic network material.

In one embodiment a vinyl ester polymer, dibutyltin oxide catalyst and at least one tri or tetraalkoxy silane are mixed and extruded into a tube with the residence time in the extruder set to extrude the material after crosslinking has begun but before an unmanageable increase in the melt viscosity of the composition occurs. The tube is formed into a balloon by a standard blowing process, suitably an axial stretch followed by radial expansion at elevated temperature into a mold. The molded balloon may optionally be held at the molding temperature or a higher temperature while pressurized at a pressure at least as high as the molding pressure to further crystallize the polymer and to facilitate the crosslinking reaction between the vinyl ester and the alkoxy silane. The balloon is then dipped in a water bath or exposed to a steam treatment for a time to hydrolyze the remaining alkoxy groups of the silane and then dried to drive condensation of the resulting silanol moieties to form a ceramic network. A low concentration of mineral acid may be incorporated into the water bath or steam supply to facilitate the hydrolysis and condensation reactions if desired.

In further embodiments the silane is a tetraalkoxy silane and/or the melt composition further includes another ceramic precursor compound as previously described, for instance a titanium or zirconium alkoxide.

In another embodiment tubing is formed as previously described and the crosslinking reaction driven further by treatment of the tubing to an elevated temperature. The elevated temperature may be from about 50° C. to about 85° C., for a period of several hours to several days, for instance a time in the range of about 4 hours to 48 hours. Suitably such treatment is performed under vacuum or with a flowing dry inert gas purge, to further drive the crosslinking reaction. After crosslinking the tubing material may be subjected to hydrolysis and condensation to give elastomeric medical device tubing.

In other embodiments the melt composition is injected into a mold under standard injection molding conditions followed by hydrolysis and condensation. Optionally the composition, after solidification, may be held at an elevated temperature inside or outside the mold under conditions as described for the previous embodiment in order to further crosslink the material before the hydrolysis and condensation is performed.

In still further embodiments of the invention, some or all of the polymer material may be a polymer having ester groups in the backbone thereof. In such case the crosslinking reaction between polymer and ceramic precursor occurs on the polymer backbone so that the polymer units become segmented. Example polymers include polyesters such as poly(ethylene terephthalate), poly(butylene terephthalate), and poly(ethylene naphthalate) and copolymers thereof; polyester-block-polyethers for instance poly(butylene terephthalate)-block-polyethers such as sold under the Hytrel® and Arnitel® trademarks; polyester urethanes; and polyamide-block-polyethers that are ester-linked such as sold under the Pebax® trademark. The products of such reactions will have particularly unique properties as a result of the incorporation of ceramic blocks at locations within the polymer backbone. The various options previously described for the vinyl ester polymer embodiments, e.g. for formulation, for shaping, for further crosslinking in the solid state, and for hydrolysis and condensation may also be employed in these embodiments.

The shaped medical device in accordance with the present invention may be an implantable or insertable medical device which is implanted or inserted either for procedural uses or as implants. Examples include balloons, catheters (e.g., renal or vascular catheters such as balloon catheters), guide wires, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, tissue bulking devices, sutures, suture anchors, anastomosis clips and rings, tissue staples and ligating clips, cannulae, orthopedic prostheses, joint prostheses, as well as various other medical devices that are adapted for implantation or insertion into the body.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim, regardless of claim sequence, if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A shaped medical device or component thereof prepared from a polymer melt composition comprising a polymer ester, a transesterification catalyst, and at least one trialkoxysilane or tetraalkoxysilane, by forming and solidifying said composition, and after solidification, subjecting the composition to reaction conditions to effect hydrolysis of at least some alkoxysilyl groups remaining in the composition to form silanol groups and to effect condensation of said silanol groups to form a ceramic network.

2. A shaped medical device or component thereof as in claim 1 wherein the polymer ester is a vinyl ester homopolymer or copolymer.

3. A shaped medical device or component thereof as in claim 2 wherein the polymer ester is a copolymer of a vinyl ester at least one other vinyl or vinylidene monomer that is not a vinyl ester.

4. A shaped medical device or component thereof as in claim 2 wherein the vinyl ester content of the copolymer may is from about 1% to about 99.5% by weight of said copolymer.

5. A shaped medical device or component thereof as in claim 1 wherein the transesterification catalyst is a member of the group comprising dialkyl tin oxides, distannoxane catalysts and mixtures thereof.

6. A shaped medical device or component thereof as in claim 1 wherein the transesterification catalyst is dibutyl tin oxide, dioctyl tin oxide or a 1-alkoxy-3-acyloxy tetraalkyldistannoxane.

7. A shaped medical device or component thereof as in claim 1 wherein the transesterification catalyst is provided to the composition in an amount of 0.5-5 mole % based on alkoxy silane groups provided to the polymer melt composition.

8. A shaped medical device or component thereof as in claim 1 wherein the polymer melt composition comprises at least one tetraalkoxysilane.

9. A shaped medical device or component thereof as in claim 8 wherein the at least one tetraallkoxysilane is tetramethoxysilane, tetraethoxysilane, tetrapropoxysilane, tetraisopropoxysilane, or a mixture thereof.

10. A shaped medical device or component thereof as in claim 8 wherein the polymer melt composition further comprises at least one trialkoxysilane.

11. A shaped medical device or component thereof as in claim 10 wherein the trialkoxysilane is a member of the group consisting of trialkoxyalkylsilanes in which the alkyl group is optionally substituted with an aromatic hydrocarbon group, with one or more halogen atoms or with an organic functional group having one or more oxygen, nitrogen or sulfur atoms thereon, trialkoxyarylsilanes in which the aryl group is unsubstituted or is substituted with an aliphatic hydrocarbon group, with one or more halogen atoms or with an organic functional group having one or more oxygen, nitrogen or sulfur atoms thereon, and mixtures thereof.

12. A shaped medical device or component thereof as in claim 1 wherein the polymer melt composition comprises a trialkoxyfluoroalkylsilane.

13. A shaped medical device or component thereof as in claim 1 wherein the polymer melt composition further comprises a ceramic precursor other than said silicon alkoxide, which is a compound of silicon, zirconium, titanium, aluminum, tin, hafnium, rubidium, bismuth, strontium, tantalum, molybdenum, tungsten, rhenium and/or iridium that can form oxides of such metals or semimetals by a hydrolysis/condensation sequence.

14. A shaped medical device or component thereof as in claim 13 wherein the ceramic precursor other than said silicon alkoxide, comprises a titanium alkoxide, zirconium alkoxide or a mixture of two or more thereof.

15. A shaped medical device or component thereof as in claim 1 wherein the polymer ester is a polymer having ester groups in the backbone thereof.

16. A shaped medical device or component thereof as in claim 15 wherein the polymer having ester groups in the backbone thereof comprises at least one member of the group consisting of polyesters, polyester-block-polyethers, polyester urethanes, and polyamide-block-polyethers that are ester-linked.

17. A shaped medical device or component thereof as in claim 1 wherein the medical device is an implantable or insertable medical device.

18. A shaped medical device or component thereof as in claim 1 wherein the medical device is a member of the group consisting of balloons, catheters, guide wires, filters, stents, stent grafts, vascular grafts, vascular access ports, embolization devices, myocardial plugs, pacemaker leads, left ventricular assist hearts and pumps, total artificial hearts, heart valves, vascular valves, tissue bulking devices, sutures, suture anchors, anastomosis clips and rings, tissue staples and ligating clips, cannulae, orthopedic prostheses, and joint prostheses.

19. A method of forming a shaped medical device or component thereof comprising
    providing a polymer melt composition comprising
        a polymer ester,
        a transesterification catalyst, and
        at least one trialkoxysilane or tetraalkoxysilane,
    forming and solidifying said composition, and after solidification,
    subjecting the composition to reaction conditions to effect hydrolysis of at least some alkoxysilyl groups remaining in the composition to form silanol groups and to effect condensation of said silanol groups to form a ceramic network.

20. A method as in claim 19 wherein the step of forming and solidifying the composition comprises extruding a tube of said polymer melt composition and the method further comprising a post-forming step which comprises blowing the tube into a medical device balloon.

21. A method as in claim 19 wherein the polymer ester is a polymer having ester groups in the backbone thereof.

22. Medical device tubing prepared from a polymer melt composition comprising a polymer ester, a transesterification catalyst, and at least one trialkoxysilane or tetraalkoxysilane, by extruding and solidifying said composition in tubing form, and after solidification, heating the tubing and subsequently subjecting the tubing to reaction conditions to effect hydrolysis of at least some alkoxysilyl groups remaining in the composition to form silanol groups and to effect condensation of said silanol groups to form a ceramic network.

23. Medical device tubing as in claim 22 wherein the polymer ester is a polymer having ester groups in the backbone thereof.

24. A medical device balloon prepared from a polymer melt composition comprising a polymer ester, a transesterification catalyst, and at least one trialkoxysilane or tetraalkoxysilane, by extruding and solidifying said composition in tubing form, forming the tubing into a balloon, and after the balloon is formed subjecting the balloon to reaction conditions to effect hydrolysis of at least some alkoxysilyl groups remaining in the composition to form silanol groups and to effect condensation of said silanol groups to form a ceramic network.

25. A medical device balloon as in claim 24 wherein the polymer ester is a polymer having ester groups in the backbone thereof.

* * * * *